United States Patent
Kreitlow

(10) Patent No.: US 7,351,853 B2
(45) Date of Patent: Apr. 1, 2008

(54) METHOD OF MANUFACTURING A GRANULAR MINERAL COMPOSITION

(75) Inventor: Robert William Kreitlow, Roy, UT (US)

(73) Assignee: Albion Advanced Nutrition, Clearfield, UT (US)

( * ) Notice: Subject to any disclaimer, the term of this patent is extended or adjusted under 35 U.S.C. 154(b) by 0 days.

(21) Appl. No.: 11/623,145

(22) Filed: Jan. 15, 2007

(65) Prior Publication Data
US 2007/0170613 A1    Jul. 26, 2007

Related U.S. Application Data

(60) Provisional application No. 60/761,147, filed on Jan. 23, 2006.

(51) Int. Cl.
    *C07C 69/63* (2006.01)

(52) U.S. Cl. .................................................. 560/230
(58) Field of Classification Search ................... None
    See application file for complete search history.

(56) References Cited

U.S. PATENT DOCUMENTS

| | | | |
|---|---|---|---|
| 5,019,148 A | 5/1991 | Moore ........................... 71/11 |
| 5,025,036 A | 6/1991 | Carson et al. ............... 514/568 |
| 5,348,745 A * | 9/1994 | Daher .......................... 424/466 |
| 5,437,873 A | 8/1995 | Phadke et al. .............. 424/465 |
| 5,817,340 A | 10/1998 | Roche et al. ................ 424/470 |
| 6,316,026 B1 | 11/2001 | Tatara et al. ................. 424/464 |
| 6,358,526 B1 | 3/2002 | Mergens et al. ............. 424/464 |
| 6,635,278 B1 | 10/2003 | Dahl et al. ................... 424/465 |
| 2004/0185087 A1* | 9/2004 | Hartle et al. ................. 424/442 |
| 2004/0197398 A1 | 10/2004 | Friesen et al. ............... 424/464 |
| 2004/0258748 A1 | 12/2004 | Madan et al. ............... 424/464 |
| 2005/0013857 A1 | 1/2005 | Fu et al. ...................... 424/464 |
| 2005/0019389 A1 | 1/2005 | Rozhon et al. .............. 424/452 |
| 2005/0031700 A1 | 2/2005 | Hall et al. ................... 424/489 |
| 2005/0037070 A1 | 2/2005 | Hall et al. ................... 424/464 |
| 2005/0080134 A1 | 4/2005 | Niddam-Hildesheim et al. ......................... 514/548 |
| 2005/0112193 A1 | 5/2005 | Phillips et al. .............. 424/464 |

FOREIGN PATENT DOCUMENTS

| | | |
|---|---|---|
| EP | 0396972 | 11/1990 |
| GB | 715874 | 9/1958 |
| JP | 56073019 | 6/1981 |
| JP | 2001031701 | 2/2001 |

OTHER PUBLICATIONS

VanKamp, et al. "Improvement by Super Disintegrants of the Properties of Tablets Containing Lactose, Prepared by Wet Granulation", Pharm Weekbl Sci., Aug. 26; 5 (4), pp. 165-171, (1983).
Tapia, et al. "Effect of Formulation and Process Variables on the Release of Behavior of Amoxicillin Matrix Tablets", Drug. Dev. Ind. Pharm, Sep. 30 (8), pp. 901-908, (2004).
Wu, et al. "Influence of Wet Granulation and Lubrication on the Powder and Tableting Properties of Codried Product of Microcrystalline Cellulose with Beta-Cyclodextrin", Eur. J. Pharm. Biopharm51 (1), ., pp. 63-69, Jan. 2001.
Chalmers, et al. "Oxytetracycline Tablet Formulations: The Influence of Excipients and the Methods of Granulation", J. Pharm. Pharmacol., Mar. 28 (3), pp. 234-238, (1976).

* cited by examiner

*Primary Examiner*—Janet L. Andres
*Assistant Examiner*—M Louisa Lao
(74) *Attorney, Agent, or Firm*—Workman Nydegger

(57) ABSTRACT

A method for forming mineral granules can be accomplished with a granulation reaction of edible acids and mineral bases to form mineral salts. The reaction is carried out in a manner that produces granules without requiring a binder or requiring the use of extrusion and milling techniques to control particle size. The granulation reaction can be performed by introducing a solvent into reaction vessel and dissolving an edible acid into the solvent before adding a first portion of a total amount of a mineral base into the reaction vessel to form a first mixture. The reaction components are then mixed and maintained at an elevated temperature below the boiling point. A final portion of the mineral base is then added into the reaction vessel, and mixed at a final temperature below the boiling point so as to induce agglutination to form granules having a dimension of at least 40 microns.

25 Claims, No Drawings

METHOD OF MANUFACTURING A GRANULAR MINERAL COMPOSITION

CROSS-REFERENCE TO RELATED APPLICATIONS

This U.S. patent application claims the benefit of U.S. Provisional Application Ser. No. 60/761,147, filed Jan. 23, 2006, the disclosure of which is incorporated herein in its entirety.

BACKGROUND OF THE INVENTION

1. The Field of the Invention

The present invention relates to methods for manufacturing a granulated product. More particularly, the present invention relates to methods of using chemical reactions that induce the formation and agglutination of particles so as to produce granules comprised of minerals.

2. The Related Technology

Granular formulations are important for use in various industries, and have been found to be particularly useful in the pharmaceutical, nutraceutical, and dietary supplement industries. Typically, these industries use granular formulations in order to produce consumable products that can be easily packaged and distributed. This includes using the granular formulations during the production of tablet and capsule medicaments that include active ingredients or for a variety of other applications. Granular formulations can be preferred because they are easy to use and handle and can be supplied into various types of manufacturing equipment. In part, the granular formulations are easy to use because they can be configured to be soluble, compactable, and tabletable and can be easily measured and delivered in accurate quantities.

In various processes it can be preferred that the granular formulation include granules that have a minimum diameter, maximum diameter, or range of diameters in order to achieve a desired functionality. As such, previous processes that prepare granular formulations have required milling or grinding solid formulations so that the desired granule particle sizes can be achieved. However, milling and grinding can be a tedious and time consuming process and can require large and expensive equipment. Also, milling and grinding techniques may also provide granular formulations that do not conform to the particle size characteristics, and may provide granules that are either too small or too large. On the other hand, inadequate milling or grinding can be especially problematic to the pharmaceutical and dietary supplement industries because of the necessity for strict compliance with various rules, regulations, and consistent product characterizations that require specific and narrow particle sizes.

Moreover, a typical process that produces a granular formulation can require a number of steps that add to complexity and cost, and may result in granular products that do not conform to specific needs. Such a process can be exemplified by wet granulation processes. A wet granulation process can include mixing an active ingredient and binder in a mixer with a granulating solution or fluid until the desired characteristics are achieved. The desired characteristics can include cohesiveness, malleability, and the ability to be extruded and/or dried.

A dried product can be milled or ground to achieve granules having a maximum particle size. Sometimes an extruded product has to be pelletized in a separate step before being introduced into a grinder or mill that can produce granules having the appropriate size. Additionally, the milling and grinding of a particulate composition can usually result in the formation of powders that contaminate the granular formulations. Even though the powder can be comprised of the same material as the granule, the small particulates can be unacceptable for tablet or capsule preparations. Additionally, particulate compositions that include powders can be difficult to handle because the powders are easily airborne and can cause measuring and delivery errors.

Another problematic process that has been developed for preparing granular formulations is referred to as spray drying granulation. In this process a fluid bed granulation system fluidizes the active ingredient, binders, and optional excipients into a fluidic stream. The fluidized suspension is then sprayed onto the top of a fluidized bed using a spray nozzle. This procedure can use a lot of energy in order to get the active ingredient into the fluidized stream. Also, this procedure can produce a lot of powders and fines that do not conform to the uses of the granular product. Moreover, the granules can be soft and may not perform well during subsequent processing.

The typical granulation processes that produce the granular products start with the active ingredient that is to be granulated. In the instances the active ingredient is a reaction product a chemical reaction may need to be performed in addition to the granulation process. Accordingly, the granulation of a reaction product can be even more complicated, time consuming, and expensive when the reaction has to be performed. Additionally, many chemical reactions produce byproducts that have to be separated from the active ingredient before it can be included in a granulation procedure.

Therefore, it would be advantageous to have an improved granulation procedure that includes fewer steps and does not necessarily require grinding, milling, or spray drying to obtain granules. Additionally, it would be beneficial to have a chemical reaction procedure that can be used in order to produce a granule formulation without requiring grinding, milling, or spray drying to obtain granules.

BRIEF SUMMARY OF THE INVENTION

Generally, the present invention includes a method of forming mineral granules by a granulation reaction. The granulation reaction uses edible acids and mineral bases to form mineral salts. The granulation reaction is carried out in a manner that produces granules without requiring a binder or requiring the use of extrusion and/or milling techniques to control particle size. The granulation reaction can be performed by introducing a solvent into a reaction vessel and dissolving an edible acid into the solvent. Subsequently, a first portion of a total amount of a mineral base, such as a mineral hydroxide, mineral oxide, and/or mineral carbonate, is added into the reaction vessel to form a first mixture. The reaction components of the first mixture are then mixed and maintained at an elevated temperature below the boiling point of the solvent. A final portion of the mineral base is then added into the reaction vessel to form a final mixture that is mixed at a final temperature below the boiling point so as to induce agglutination and form granules. The final mixture is processed until the desired granule size is achieved.

In one embodiment, the solvent can be an aqueous solution. Various solvents can be combined with water in order to from an aqueous solution. Examples of such solvents can be organic solvents with high volatility that can be easily removed without boiling water. Additionally, various salts can be included within the aqueous solution. In one embodiment, the edible acid can be selected from the group consisting of malic acid, fumaric acid, citric acid, lactic acid, benzoic acid, tartaric acid, adipic acid, succinic acid, acetic acid, phosphoric acid, propionic acid, sulfuric acid, and combinations thereof.

In one embodiment, the edible acid can be an organic acid. Organic acids that can be used in the present invention can be selected from the group consisting of malic acid, fumaric acid, citric acid, lactic acid, benzoic acid, tartaric acid, adipic acid, succinic acid, acetic acid, propionic acid, and combinations thereof. Preferably, the granulation reaction includes malic acid and/or citric acid to form mineral malates and/or mineral citrates.

In one embodiment, the mineral base can be a mineral hydroxide, mineral oxide, and/or mineral carbonate. The mineral bases can include bases of potassium, magnesium, calcium, and combinations thereof, which can react with an acid to form a salt. Also, the mineral base can be an alkali or alkaline earth hydroxide, oxide, and/or carbonate. Also, any mineral that can be present as a base that reacts with the edible acid in order to form an edible salt form of the mineral can be used. Preferably, the mineral can be used as a food fortificant. Examples of minerals that can also be used include mono, di, or trivalent cationic metals such as calcium, magnesium, manganese, iron, copper, zinc, potassium, cobalt, chromium, molybdenum, vanadium, sodium, phosphorus, selenium, lithium, rubidium, cesium, francium, and the like.

In one embodiment, the first portion of mineral base can be at least about 20% of the total amount that is added to the granulation reaction to form the mineral granules. Also, the first portion can be less than 60% of the total amount. Preferably, the first portion is between about 25% to about 40% of the total amount of mineral base.

In one embodiment, the amount and procedure for adding the mineral base can be modulated in order to produce a desired granular product from the reaction. As such, it can be preferable in some instances for the first portion to be added in bulk. Alternatively, the first portion can be added in a substantially continuous or intermittent flow. Similarly, the final portion can be added in bulk, or as a continuous or intermittent flow. Also, the rate or duration in which the mineral base is added can be modulated as needed to produce granules of a desired size.

In one embodiment, the mineral base can be added in a manner that allows for an exothermic reaction with the edible acid to take place. As such, the heat generated by the exothermic reaction can be used to heat the reaction mixture in order to drive the water off by evaporation as well as absorption into the matrix of the agglutinated particles. Also, the mineral base can be added to the reaction in a controlled process that allows for the temperature to be controlled, wherein the controlled process can be incremental bulk additions or a controlled continuous or intermittent flow of at various rates. Also, the amount of mineral base can be modulated and varied in order to keep the temperature within a proper range and to prevent the reactants from baking or burning onto the reaction vessel or charring the granular reaction product.

In one embodiment, the granulation reaction can produce granules at a desired size without extrusion or milling. As such, the reaction causes particles of mineral salts to agglutinate to produce granules having the desired size. During the agglutination process water can be bound within the granule matrix or evaporated. This can cause the water in a free and liquid form to be substantially removed from the granulation reaction so as to produce solid granules without a significant amount of free water.

In one embodiment, the granules can be characterized as preferably being from about 20 mesh to about 325 mesh. More preferably, the granules can be characterized as being from about 20 mesh to about 220 mesh, and most preferably from about 60 mesh to about 80 mesh.

In one embodiment, the granulation reaction produces a total amount of granules being less than 300 kg. More preferably, the total amount of granules is less than 250 kg. Even more preferably, the total amount of granules is less than 200 kg. Most preferably, the total amount of granules is less than 180 kg.

In one embodiment, the first temperature is less than the final temperature, and the first temperature of the granulation reaction is maintained below the boiling point of the solvent. Additionally, the first temperature can be less than about 40° C., more preferably less than about 35° C., most preferably less than about 30° C. In any event, the temperature of the reaction vessel throughout the process should be kept sufficiently low throughout the reaction to prevent a reactant from becoming baked or burnt onto the reaction vessel. Accordingly, the final temperature can be less than about 100° C., more preferably less than about 80° C., even more preferably less than about 70° C., still more preferably less than about 60° C., and most preferably less than about 50° C.

In one embodiment, a second portion of the total amount of the mineral base can be introduced into the reaction vessel to form a second mixture. The second mixture can be substantially similar to the first mixture, except that it can have a higher concentration of mineral. The granulation reaction can be continued with the additional mineral base by maintaining the second mixture at a second temperature that is below the boiling point of the solvent while mixing the second mixture. The second temperature can be maintained by a temperature control reaction vessel or by modulating the process and/or rate of adding the second portion. Moreover, a third, fourth, or fifth through $N^{th}$ portion of the total amount of mineral base can be added at subsequent intervals similar to the manner of adding the first and/or second portion of mineral base.

In one embodiment, the consistency, flowability and/or mixability of the reaction mixture second portion can be modulated to vary from a slurry through its solidification as granules. That is, the reaction mixture can begin to slurry and continue to agglutinate and drive off free liquid water so that the consistency, flowability, and/or mixability can become a paste or dough-like, and can even become more solid. Optionally, the consistency of the reaction mixture can be changed from a liquid to a slurry, to a granular composition by maintaining the second mixture at a second temperature that is higher than the first temperature, but lower than the final temperature.

In one embodiment, the combined first and second portions of mineral base can be less than about 90% of the total amount of mineral base. Also, the combined first and second portions can be less than about 80% of the total amount. Preferably, the combined first and second portions are less than about 70% of the total amount. More preferably, the combined first and second portions are less than about 60% of the total amount. Alternatively, the combined first and second portions are greater than about 50% of the total amount.

In one embodiment, the present invention includes another method of using a chemical reaction for forming mineral granules through a granulation reaction. The granulation reaction can include introducing water into the reaction vessel, and dissolving at least one organic acid into the water. The organic acid can be substantially similar as described in more detail below. A first portion of a total amount of a mineral base in the form of a hydroxide, oxide, or carbonate is then introduced into the reaction vessel to form a first mixture, which is mixed at a first temperature that is below 100° C. Subsequently, a second though last portion of the total amount of the mineral base is added into the reaction vessel to form a final mixture. The final mixture is mixed at a final temperature that is below 100° C., however, the final temperature can be elevated so as to induce agglutination and to form granules. The process can continue until the liquid water is removed from the granules, either by absorption, incorporation into the agglutinated matrixes, or by evaporation without being boiled.

In one embodiment, the present invention can include still another method of using a chemical reaction for forming mineral granules by a granulation reaction. The granulation reaction can include introducing water into the reaction vessel, and dissolving malic acid and citric acid into the water. A first portion of mineral base is then added into the reaction vessel to form a first mixture, wherein the mineral base can be at least one of potassium hydroxide, magnesium hydroxide, calcium hydroxide, potassium oxide, magnesium oxide, calcium oxide, potassium carbonate, magnesium carbonate, or calcium carbonate. The first mixture can then be mixed at a first temperature that is below 100° C. Subsequently, a second portion of the mineral base is added into the reaction vessel to form a second mixture, which includes an increased concentration of mineral. The second mixture is then mixed at a second temperature that is below 100° C. and above the first temperature. A final portion of the mineral base is then added into the reaction vessel by bulk addition to form a final mixture. The final mixture is mixed at a final temperature range below 100° C. so as to induce agglutination to form granules, and to remove liquid water from the granules.

These and other embodiments and features of the present invention will become more fully apparent from the following description and appended claims, or may be learned by the practice of the invention as set forth hereinafter.

DETAILED DESCRIPTION OF THE PREFERRED EMBODIMENTS

Generally, the present invention includes a system and process for forming mineral granules by a granulation reaction. The granulation reaction uses edible acids and mineral bases to form mineral salts. The granulation reaction is carried out in a manner that produces granules without requiring a binder or requiring the use of extrusion and milling techniques to control particle size.

The granulation reaction can be performed by introducing a solvent into reaction vessel and dissolving an edible acid into the solvent before adding a first portion of a total amount of a mineral base, such as a mineral hydroxide, mineral oxide, and/or mineral carbonate, into the reaction vessel to form a first mixture. The reaction components are then mixed and maintained at an elevated temperature below the boiling point. A second through final portion of the mineral base is then added into the reaction vessel, and mixed at a final temperature below the boiling point so as to induce agglutination to form granules.

I. Reactants

Generally, the granulation reaction includes reactants that can react in a manner that induces the formation of particles that can agglutinate into granules of a desired size. As such, the reactants can include a solvent that can solubilize both an edible acid and a mineral base. Also, the solvent can be incorporated into the agglutinated granules so it may be favorable to have a physiologically acceptable solvent that can be used in pharmaceuticals, nutraceuticals, or dietary supplements. Additionally, the solvent may need to be capable of being vaporized and evaporated from the granulation reaction without requiring enough heat to cause the other reactants to bake or burn onto the reaction vessel.

In one embodiment, the solvent can be an aqueous solution Comprising a water mixture. Also, the solvent can consist of only water. Water is a preferred solvent because it can be incorporated into a granule without any undue consequences that prevent the granule from being used in an edible preparation. Additionally, water can be easily evaporated at temperatures that do not bake or burn the other reactants onto the reaction vessel. However, it is preferred that the reaction conditions be kept at a temperature less than 100° C. or other temperature so that the water does not boil. As such, the composition of the aqueous solution can be modulated in order to control the rate of evaporation or boiling so that the components do not bake or burn.

Additionally, other solvents can be combined with water in order to from an aqueous solution. Examples of such solvents can be organic solvents with high volatility that can be easily removed without boiling water. Alcohols, such as ethanol or isopropanol, can be used in place of water or combined therewith to provide a suitable solvent. However, ethanol or other edible solvents can be advantageous. Additionally, various salts can be included within the aqueous solution.

In one embodiment, the edible acid can be any type of acidic compound that can be used in a pharmaceutical, nutraceutical, or dietary supplement formulation. Edible acids are suitable to be used with basic minerals so that an acid-base reaction can be conducted to form a mineral salt. Also, it is preferred that the acid be edible so that the granular formulations are suitable for use in any food or beverage preparation or other consumable product. Additionally, the use of materials that produce products or byproducts that can be used in foods can greatly simplify the synthesis protocols that otherwise may require additional separation steps so that unfavorable or unwanted byproducts can be removed. Thus, edible acids can be used in order to prepare a mineral salt that can be used in a variety of applications. Examples of edible acids include malic acid, fumaric acid, citric acid, lactic acid, benzoic acid, tartaric acid, adipic acid, succinic acid, acetic acid, phosphoric acid, propionic acid, sulfuric acid, various amino acids, and combinations thereof. Additionally, the edible acid can be an organic acid that is commonly used in various food preparations.

In one embodiment, the present invention uses a basic mineral to produce a mineral granule. The basic mineral can be any alkaline mineral with a high pH that is reactive with an acid in order to form a salt. It is preferred that the mineral be a physiologically active mineral that is used in a biological process or recommended to be consumed for heath purposes. Examples of minerals that can be used include mono, di, or trivalent cationic metals such as calcium, magnesium, manganese, iron, copper, zinc, potassium, cobalt, chromium, molybdenum, vanadium, sodium, phosphorus, selenium, lithium, rubidium, cesium, francium, and the like. Accordingly, any beneficial mineral that can be provided as a base can be used in the present invention in order to prepare mineral granules.

In one embodiment, the basic mineral can be a mineral hydroxide, mineral oxide, mineral carbonate and/or the like. Examples of mineral bases can include potassium, magnesium, calcium, and combinations thereof in the form of hydroxides, oxides, carbonate and like basic components. Also, the mineral base can be an alkali or alkaline earth base. In some instances it can be preferably for the mineral base to be a mineral hydroxide. In other instances either mineral oxides or mineral carbonates can be preferred depending on the product that is desired.

The present invention can produce mineral granules without the use of a binder by performing the granulation reaction described herein. However, the granulation reaction can also include other ingredients besides the solvent, edible acid, and basic mineral. As such, the additional ingredients that can be included are those that do not interfere with or inhibit the granulation reaction. Examples of other ingredients include binders, lubricants, surfactants, effervescent substances, fillers, and other well known substances that can be used to prepare pharmaceuticals, nutraceuticals, and/or dietary supplements.

II. Reaction Granules

The present invention includes granules comprised of a mineral that can be used to prepare pharmaceuticals, nutraceuticals, and/or dietary supplements. Accordingly, the granules can be comprised of a mineral salt that is edible. The granules can be characterized by having desirable physical characteristics, such as adequate hardness, dissolution, content uniformity, and the like, for being used to form tablets or capsules. This can include a hardness that enables the granules to be stably pressed into tablets without breaking or turning into a powder. Also, the granules can be used in ready-mix beverage formulations. Thus, the granules can have suitable characteristics for being used in a variety of consumable goods.

It is preferred that the reactants be added in proper stoichiometric amounts so that all of the reactants are used. However, the granules can be formed to include various amounts of unreacted edible acid and/or unreacted mineral base. Preferably, the granules have a substantially consistent composition within each granule and between different granules, but non-uniform granules can also be prepared.

In one embodiment, the granules can be prepared to have a wide range of sizes and shapes. Usually, the granules are substantially spherical; however, agglutination can create granules that have various shapes and sizes. Additionally, the agglutination reaction can be controlled in order to produce granules having desired size limitations. For example, the agglutination can be continued to produce granules that have a size so as to not pass through 325 mesh, more preferably through 220 mesh, even more preferably through 180 mesh, and most preferably 80 mesh. Alternatively, the granules can be characterized as having a size being between about 20 mesh to about 220 mesh, more preferably between about 40 mesh and 180 mesh, even more preferably between 50 mesh and 100 mesh, and most preferably between about 60 mesh to about 80 mesh. In some instances, the granule size can be greater than about 80 mesh, 60 mesh, 40 mesh, or even 20 mesh depending on the intended use.

In one embodiment, the granules can have a dimension of at least about 40 microns. That is, the granule can have a dimension (e.g. diameter, width, length, and/or height) that is at least about 40 microns. Preferably, the dimension can be at least about 80 microns, more preferably at least about 100 microns, even more preferably, at least about 200 microns, still more preferably at least about 225 microns, and most preferably at least about 250 microns. However, some agglutinated granules can be over 1 mm in any dimension.

III. Granulation Reaction

In one embodiment, the present invention includes a method for forming mineral granules that can be accomplished with a granulation reaction of edible acids and mineral bases to form mineral salts. The granulation reaction can be carried out in a manner that produces granules without requiring a binder or requiring the use of extrusion and milling techniques to control particle size. The granulation reaction can be performed by introducing a solvent into the reaction vessel and dissolving an edible acid into the solvent before adding a first portion of a total amount of a basic mineral into the reaction vessel to form a first mixture. The reaction components are then mixed and maintained at an elevated temperature below the boiling point. A final portion of the basic mineral is then added into the reaction vessel, and mixed at a final temperature below the boiling point so as to induce agglutination to form granules having a desired size, such as a dimension of at least 40 microns.

A first phase of the granulation reaction can be performed by dissolving an edible acid in water to form an aqueous acidic solution, which can take from 5 to 20 minutes depending on the acid. Usually, the reaction is performed in an open mixer, which can be in a ribbon blender with or without a means for maintaining a constant temperature; however, a controlled environment or closed mixer reaction vessels can also be used.

A first portion of a mineral base can be added to the aqueous acid solution in incremental amounts or as a slow continuous supply over a first time period to form a reaction mixture. During the first time period, the temperature can be increased to a first temperature, which is maintained relatively constant, such as about +/−50 degrees, at a temperature at or below boiling in order to keep the reagents in solution. Preferably, the temperature is maintained at a constant temperature within about +/−35 degrees, more preferably within about +/−25 degrees, and most preferably within about +/−10 degrees. The temperature can be controlled by controlling the temperature of the mixer, or by controlling the rate and/or amount of mineral base added to the aqueous acid solution.

In one embodiment, an optional second phase of the granulation reaction can be performed by adding a second portion of the mineral base to the reaction mixture. The second portion can be added in a manner substantially similar as the first portion. Optionally, the second portion of the mineral base induces the reaction mixture to begin to solidify or increase in viscosity so as to become a slurry, paste, or dough-like substance. Alternatively, the reaction composition can be maintained as a solution or slurry during this process. The optional second phase can be performed under substantially the constant temperature conditions of the first phase, but can be at a temperature higher than the first temperature due to the exothermic reaction.

After the first phase or optional second phase, the final phase of the granulation reaction can be performed by adding a final portion of the mineral base to the reaction mixture. The reaction mixture can have a consistency ranging from liquid to dough-like particles. The final portion of the mineral base can be added to the reaction composition in bulk, incremental amounts, or as a slow continuous supply over a final time period. During the final time period, the final temperature range can be increased to a temperature that is higher than the first or second temperatures, but below or about the boiling point so as to drive the granulation. Optionally, the final temperature range can be increased to at or above the boiling point, but maintained so that the reagents do not bake or burn onto the reaction vessel. The final temperature range can be controlled by controlling the temperature of the mixer, or by controlling the rate and amount of the final portion of the mineral base being added to the reaction composition.

During the final phase, the reaction products can agglutinate so as to form granules in the mixer. The product can be reacted until the water has been expelled or incorporated into the granules; however, subsequent heating and/or drying can be performed to remove the rest of the water from the granules. Usually, the granules have less then 10% or preferably less than 6% of water when granulated and dried. Also, the granular composition can be substantially free of fines so as to not be powdery. Thus, the granulation reaction can allow for the formation of granules of a desired size without spray drying and/or extrusion and pelletization. Also, the granulation reaction can result in a granular composition with highly agglutinated granules.

The size and constancy of the granules are suitable for preparing tablets, capsules, or the like, with or without supplementary materials. The granules can be prepared in a variety of sizes such as those described herein. Optionally, the granulation reaction can produce agglutinated granules having sizes larger then 325 mesh. Additionally, the reaction product can be characterized as a mineral salt, such as a mineral citrate, mineral malate, or mineral amino acid, which can optionally be a mineral chelate. For example, when the mineral hydroxide is calcium hydroxide and organic acids are malic acid and citric acid, the granulation reaction can produce granules of calcium citrate malate.

In one embodiment, the first reaction temperature is less than the final reaction temperature, and the temperature of the granulation reaction can be maintained below the boiling point of the solvent. However, some boiling can be allowed as long as the reactants or granules do not bake or burn. Accordingly, when water is the solvent, the final temperature can be less than about 100° C., more preferably less than about 80° C., even more preferably less than about 70° C., still more preferably less than about 60° C., and most preferably less than about 50° C. Additionally, the first temperature can be less than about 40° C., more preferably less than about 35° C., most preferably less than about 30° C. In any event, the temperature of the reaction vessel should be kept sufficiently low throughout the reaction to prevent a reactant from baking or burning onto the reaction vessel.

In one embodiment, the amount and procedure for adding the mineral base can be modulated in order to produce granular products that have different sized granules. As such, it can be preferable in some instances for the first portion to be added in bulk. Alternatively, the first portion can be added in a substantially continuous flow. Similarly, the subsequent portions and/or final portion can be added in bulk, or as a continuous flow. Also, additional amounts of the edible acid can be added at any time throughout the granulation reaction as needed or desired.

In one embodiment, the mineral base can be added in a manner that allows for an exothermic reaction with the edible acid to take place. As such, the heat generated by the exothermic reaction can be used to heat the reaction mixture in order to drive off the water by evaporation as well as absorption into the matrix of the agglutinated particles. Also, the mineral base can be added to the reaction in a controlled process that allows for the temperature to be controlled, wherein the controlled process can be incremental bulk additions, a controlled continuous flow or the like. Also, the amount of mineral base can be modulated and varied in order to keep the temperature within a proper range and to prevent the reactants or granules from baking or burning onto the reaction vessel or charring the granular reaction product.

In one embodiment, the granulation reaction can produce granules without extrusion or milling. As such, the reaction causes particles of mineral salts to agglutinate to produce granules. During the agglutination process water can be bound within the granule matrix and evaporations. This can cause the water in a free and liquid form to be substantially removed from the granulation reaction to produce solid granules without a significant amount of free water at the end of the granulation reaction. Also, the water may absorb into the granules during agglutination.

In one embodiment, at least a second portion of the total amount of the mineral base is introduced into the reaction vessel to form a second mixture. The second mixture is substantially similar to the first mixture, except that it has a higher concentration of mineral. The granulation reaction is continued after the addition of additional mineral base by maintaining the second mixture at a second temperature below the boiling point of the solvent while mixing the second mixture. The second temperature can be maintained by a temperature control reaction vessel or by modulating the process of adding the at least second portion. Moreover, a third, fourth, or fifth through $N^{th}$ portion of the total amount of mineral base can be added at subsequent intervals similar to the manner of adding the second portion of mineral base.

In one embodiment, the consistency of the reaction mixture second portion can be induced to vary from a slurry through its solidification as granules. That is, the reaction mixture can begin to slurry and continue to agglutinate and drive off free liquid water so that the consistency of the granules can become like a paste or dough-like, and can even become a more solid form of granules. Optionally, the consistency of the reaction mixture can be changed from a liquid to a paste or granular slurry by maintaining the second mixture at a second temperature that is higher than the first temperature, but lower than the final temperature.

In one embodiment, the combined first and second portions which can include all portions except the final portion, are less than about 90% of the total amount. Also, the combined first and second portions are less than about 80% of the total amount. Preferably, the combined first and second portions are less than about 70% of the total amount. More preferably, the combined first and second portions are less than about 60% of the total amount. Alternatively, the combined first and second portions are greater than about 50% of the total amount. Accordingly, the final portion can be less than about 40% of the total amount, more preferably less than 30% of the total amount, even more preferably less than 20% of the total amount, and most preferably less than 10% of the total amount.

In one embodiment, the first portion of mineral base can be at least about 20% of the total amount that is added to the granulation reaction to form the mineral granules. Also, the first portion can be less than 60% of the total amount. Preferably, the first portion is between about 25% to about 40% of the total amount of mineral base. In the instance multiple portions of mineral base are added before the final portion, it can be preferred that the portions be substantially equal in amount. For example, when three total portions are added, it is preferred that the first, second, and final portions each be about 33.3% of the total amount of mineral base.

In one embodiment, it is preferred that the final portion be added in bulk so that the exothermic reaction drives the granulation and agglutination as well as drives the water from being in a free liquid form.

The present inventive granulation reaction can be scaled to produce any amount of product in a batch reaction. As such, the amount of volume of granules obtained by the granulation reaction can be modulated by changing the volume of the reaction vessel as well as the amount of reactants.

In one embodiment, the granulation reaction produces a total amount of granules being less than 300 kg. More preferably, the total amount of granules is less than 250 kg. Even more preferably, the total amount of granules is less than 200 kg. Most preferably, the total amount of granules is less than 180 kg.

EXAMPLES

The following examples are provided to describe some embodiments of the present invention in a manner that can be use by one of skill in the art to practice the present invention.

Example 1

A granulation reaction was performed to prepare a granular formulation of calcium citrate malate. The granulation reaction procedure was initiated by adding 70 lbs (about 31.6 kg) of water into a ribbon blender having a reaction void of about 50 ft$^3$ (about 1415 L), where the water had a temperature of about 64° F. (about 17.7° C.). About 68.4 lbs (about 31 kg) of citric acid and about 71.6 lbs (about 32.5 kg) of malic acid were sequentially added to the water. The ribbon blender was activated to stir the mixture for about 5 minutes and the mixture was cooled to about 43° F. (about 6.1° C.). About 25 lbs (about 11.34 kg) of calcium hydroxide was then added to the mixture by bulk addition, which was about 31.5% of the total amount of calcium hydroxide added to the granulation reaction. The temperature was increased to about 97° F. (about 36.1° C.) by an exothermic reaction, and the mixture was mixed for 5 minutes. Another bulk addition of about 25 lbs (about 11.34 kg) of calcium hydroxide was added to the reaction mixture, and the temperature was increased to about 138° F. (about 58.9° C.) by an exothermic reaction. The mixture was in a liquid state, and was mixed until the temperature began to decrease. Another bulk addition of about 25 lbs (about 11.34 kg) of calcium hydroxide was added to the reaction mixture, and the temperature was increased to about 160° F. (about 71.1° C.) by an exothermic reaction. The mixture began to agglutinate and form a slurry of granules, and the final bulk addition of about 4.13 lbs (about 1.87 kg) of calcium hydroxide was added to the reaction mixture and mixed for about 9 minutes. The temperature was maintained at about 160° F. (about 71.1° C.) while being mixed, and started to cool to about 110° F. (about 43.3° C.) as the reaction was completed. During the final phase, the liquid water in the ribbon blender disappeared. While steam was observed, it probably did not account for the amount and rate the liquid water disappeared from the reaction mixture. Thus, it is assumed that some of the water is incorporated into the agglutinated matrix of the granules. The results of the reaction formed about 200 lbs (about 90.7 kg) of calcium citrate malate granules.

Example 2

A granulation reaction was performed to prepare a granular formulation of calcium citrate malate. The granulation reaction procedure was initiated by adding 287 lbs (about 130 kg) of water into the ribbon blender of Example 1, where the water had a temperature of about 64° F. (about 17.7° C.). About 293.56 lbs (about 133 kg) of citric acid and about 280.44 lbs (about 127.2 kg) of malic acid were simultaneously added to the water. The ribbon blender was activated to stir the mixture for about 5 minutes. About 87.22 lbs (about 39.6 kg) of calcium hydroxide was then added to the mixture by bulk addition, and another bulk addition of 75 lbs (about 34 kg) was added 6 minutes later. The temperature was increased to about 165° F. (about 73.9° C.) by an exothermic reaction, and the mixture was mixed for 5 minutes while still a liquid. The last bulk addition of about 162 lbs (about 73.5 kg) of calcium hydroxide was added to the reaction mixture, and the temperature rapidly increased so that too much steam came out. After 20 minutes of mixing, the reaction temperature decreased and a granular product was obtained. A lot of the reaction product stuck to the walls and lid of the blender.

Example 3

The granulation reaction includes introducing water into reaction vessel, and dissolving malic acid into the water. A first portion of a total amount of a magnesium hydroxide is then into the reaction vessel to form a first mixture, which is then maintained at a first temperature below 100° C. while mixing the first mixture. Subsequently, a last portion of the total amount of the magnesium hydroxide is added into the reaction vessel to form a final mixture. The final mixture is mixed at a final temperature that below 100° C., but is elevated so as to induce agglutination and to form granules having a dimension of at least 40 microns. The process continues until the liquid water is removed from the granules, which can be by being absorbed or incorporated into the agglutinated matrixes or by evaporation without being boiled. The product is expected to be a magnesium malate.

Example 4

The granulation reaction includes introducing water into the reaction vessel, and dissolving citric acid into the water. A first portion of potassium hydroxide is then added into the reaction vessel to form a first mixture. The first mixture is mixed at a first temperature below 100° C. Subsequently, a second portion of the potassium hydroxide is added into the reaction vessel to form a second mixture, which includes an increased concentration of potassium. The second mixture is then mixed at a second temperature below 100° C. and above the first temperature. A final portion of the mineral hydroxide is then added into the reaction vessel by bulk addition to form a final mixture. The final mixture is mixed at a final temperature range below 100° C. so as to induce agglutination to form granules having a dimension of at least 40 microns, and to remove liquid water from the granules. The product is expected to be a potassium citrate.

Example 5

A granulation reaction is performed to prepare a granular formulation of calcium citrate malate. The granulation reaction procedure is initiated by adding about 70 lbs (about 31.6 kg) of water into a ribbon blender having a reaction void of about 50 ft³ (about 1415 L). About 68.4 lbs (about 31 kg) of citric acid and about 71.6 lbs (about 32.5 kg) of malic acid is sequentially added to the water. The ribbon blender is activated to stir the mixture for about 5 minutes. About 25 lbs (about 11.34 kg) of calcium carbonate is added to the mixture by bulk addition, which was about 31.5% of the total amount of calcium carbonate added to the granulation reaction. The temperature is increased to about 100° F. by an exothermic reaction and mixed for 5 minutes. Another bulk addition of about 25 lbs (about 11.34 kg) of calcium carbonate is added to the reaction mixture, and the temperature is increased to about 140° F. by exothermic reaction. Another bulk addition of about 25 lbs (about 11.34 kg) of calcium carbonate is added to the reaction mixture, and the temperature is increased to about 160° F. by exothermic reaction. The final bulk addition of about 4.13 lbs (about 1.87 kg) of calcium carbonate is added to the reaction mixture and mixed for about 9 minutes. The temperature is maintained at about 160° F. (about 71.1° C.) while being mixed. It is expected that the reaction will start to cool after the exothermic reaction nears complexion so that the reaction mixture obtains a temperature of about 110° F. (about 43.3° C.). It is expected that the reaction will form about 200 lbs (about 90.7 kg) of calcium citrate malate granules.

Example 6

The granulation reaction includes introducing water into reaction vessel, and dissolving malic acid into the water. A first portion of a total amount of a calcium oxide is then into the reaction vessel to form a first mixture, which is then maintained at a first temperature below 100° C. while mixing the first mixture. Subsequently, a last portion of the total amount of the calcium oxide is added into the reaction vessel to form a final mixture. The final mixture is mixed at a final temperature that below 100° C., but is elevated so as to induce agglutination and to form granules having a dimension of at least 40 microns. The process continues until the liquid water is removed from the granules, which can be by being absorbed or incorporated into the agglutinated matrixes or by evaporation without being boiled. The product is expected to be a calcium malate.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for using a controlled exothermic granulation reaction to form mineral granules, the method comprising:
   introducing a solvent into a reaction vessel;
   dissolving at least one edible acid into the solvent to form an edible acid solution in the reaction vessel;
   introducing a first portion of a total amount of a mineral base into the reaction vessel to form a first mixture in which the first portion of the mineral base reacts exothermically with a first portion of the edible acid solution to generate heat within the reaction vessel;
   mixing the first mixture while at a temperature below the boiling point of the solvent;
   introducing a last portion of the total amount of the mineral base into the reaction vessel to form a final mixture in which the last portion of the mineral base reacts exothermically with a last portion of the edible acid solutions to generate additional heat within the reaction vessel and increase solids concentration relative to the solvent; and
   mixing the final mixture to form granules of a salt of the mineral base and edible acid having a desired dimension, the final mixture being mixed at a temperature so as to prevent a solid from becoming baked or burnt onto the reaction vessel.

2. A method as in claim 1, wherein the solvent is an aqueous solution comprised of water and at least one organic solvent.

3. A method as in claim 1, wherein the first portion of the mineral base is at least about 20% of the total amount.

4. A method as in claim 1, wherein the total amount of mineral base added to the reaction vessel is less than 300 kg.

5. A method as in claim 4, wherein the average dimension of the granules is at least about 40 microns.

6. A method as in claim 1, wherein the edible acid is selected from the group consisting of malic acid, fumaric acid, citric acid, lactic acid, benzoic acid, tartaric acid, adipic acid, succinic acid, acetic acid, phosphoric acid, propionic acid, sulfuric acid, and combinations thereof.

7. A method as in claim 1, wherein the edible acid is an organic acid.

8. A method as in claim 7, wherein the organic acid is selected from the group consisting of malic acid, fumaric acid, citric acid, lactic acid, benzoic acid, tartaric acid, adipic acid, succinic acid, acetic acid, propionic acid, and combinations thereof.

9. A method as in claim 8, wherein the organic acid includes malic acid and citric acid.

10. A method as in claim 1, wherein the first mixture is mixed at a first temperature that is less than a final temperature at which the final mixture is mixed.

11. A method as in claim 10, wherein the final temperature is less than about 100° C.

12. A method as in claim 10, wherein the first temperature is less than about 50° C.

13. A method as in claim 1, wherein the mineral base is selected from the group consisting of mineral hydroxides, mineral oxides, mineral carbonates, and combinations thereof.

14. A method as in claim 13, wherein the mineral base is selected from the group consisting of calcium, magnesium, manganese, iron, copper, zinc, potassium, cobalt, chromium, molybdenum, vanadium, sodium, phosphorus, selenium, lithium, rubidium, cesium, francium, and combinations thereof.

15. A method as in claim 13, wherein the mineral hydroxide is at least one of an alkali hydroxide or an alkaline earth hydroxide.

16. A method as in claim 1, wherein the granules are characterized as being larger than about 325 mesh.

17. A method as in claim 1, wherein the first portion and/or final portion is added in a substantially continuous flow.

18. A method as in claim 1, wherein the first portion and/or final portion is added in bulk.

19. A method as in claim 1, further comprising:
   introducing a second portion of a total amount of a mineral base into the reaction vessel to form a second mixture; and
   mixing the second mixture at a temperature below the boiling point of the solvent.

20. A method as in claim 19, wherein the second mixture is mixed at a second temperature that is higher than a first temperature at which the first mixture is mixed and lower than a final temperature at which the final mixture is mixed.

21. A method as in claim 19, wherein the combined first and second portions are less than about 90% of the total amount.

22. A method as in claim 1, further comprising removing liquid from the final mixture.

23. A method as in claim 1, wherein the mineral base and edible acid exothermically react to form a salt.

24. A method for using a controlled exothermic granulation reaction to form mineral granules, the method comprising:
 introducing water into reaction vessel;
 dissolving at least one organic acid into the water to form an aqueous edible acid solution in the reaction vessel;
 introducing a first portion of a total amount of a mineral base into the reaction vessel to form a first mixture in which the first portion of the mineral base reacts exothermically with a first portion of the edible acid solution to form a salt and generate heat within the reaction vessel, wherein the mineral base is selected from the group consisting of a mineral hydroxide, mineral oxide, mineral carbonate, and combinations thereof;
 mixing the first mixture at a temperature below about 100° C.;
 introducing a last portion of the total amount of the mineral base into the reaction vessel to form a final mixture in which the last portion of the mineral base reacts exothermically with a last portion of the edible acid solution to form additional salt, generate additional heat within the reaction vessel, and increase solids concentration relative to the solvent; and
 mixing the final mixture at a temperature below about 100° C. so as to form granules of the salt formed by mixing the mineral base and edible acid having a dimension of at least about 40 microns, and to remove liquid water from the granules.

25. A method for using a controlled exothermic granulation reaction to form mineral granules, the method comprising:
 introducing water into reaction vessel;
 dissolving malic acid and citric acid into the water to form a mixed acid solution in the reaction vessel;
 introducing a first portion of a total amount of a mineral base into the reaction vessel to form a first mixture in which the first portion of the mineral base reacts exothermically with a first portion of the mixed acid solution to form a salt and generate heat within the reaction vessel, the mineral base being at least one of potassium hydroxide, magnesium hydroxide, calcium hydroxide, potassium oxide, magnesium oxide, calcium oxide, potassium carbonate, magnesium carbonate, or calcium carbonate;
 mixing the first mixture at a first temperature;
 introducing a second portion of a total amount of the mineral base into the reaction vessel to form a second mixture in which the second portion of the mineral base reacts exothermically with a second portion of the mixed acid solution to form additional salt, generate additional heat within the reaction vessel, and increase concentration of solids relative to the solvent;
 mixing the second mixture at a second temperature above the first temperature;
 introducing a last portion of the total amount of the mineral base into the reaction vessel by bulk addition to form a final mixture in which the last portion of the mineral base reacts exothermically with a last portion of the mixed acid solution to form more salt, further generate heat within the reaction vessel, and further increase concentration of solids relative to the solvent; and
 mixing the final mixture at a final temperature so as to form granules of the salt formed by mixing the mineral base, malic acid and citric acid having a desired dimension and to remove free liquid water from the granules.

* * * * *

UNITED STATES PATENT AND TRADEMARK OFFICE
CERTIFICATE OF CORRECTION

| | |
|---|---|
| PATENT NO. | : 7,351,853 B2 |
| APPLICATION NO. | : 11/623145 |
| DATED | : April 1, 2008 |
| INVENTOR(S) | : Robert William Kreitlow |

It is certified that error appears in the above-identified patent and that said Letters Patent is hereby corrected as shown below:

<u>Title Page</u>
Item (57) Abstract Line 7, change "solvent into reaction vessel" to -- solvent into a reaction vessel --

<u>Column 3</u>
Line 56, remove "at"

<u>Column 7</u>
Line 7, change "preferably" to -- preferable --

<u>Column 12</u>
Line 27/28, change "water into reaction vessel" to -- water into a reaction vessel --
Line 30, change "then into" to -- then placed into --
Line 35, change "that below" to -- that is below --

<u>Column 13</u>
Line 12, change "by exothermic" to -- by an exothermic --
Line 15, change "by exothermic" to -- by an exothermic --
Line 28/29, change "water into reaction vessel" to -- water into a reaction vessel --
Line 30, change "then into" to -- then placed into--
Line 36, change "that below" to -- that is below --

<u>Column 15</u>
Line 13, change "water into reaction vessel" to -- water into a reaction vessel --
Line 14, "formo" to -- form --

UNITED STATES PATENT AND TRADEMARK OFFICE
CERTIFICATE OF CORRECTION

PATENT NO.        : 7,351,853 B2
APPLICATION NO.   : 11/623145
DATED             : April 1, 2008
INVENTOR(S)       : Robert William Kreitlow It is certified that error appears in the above-identified patent and that said Letters Patent is hereby corrected as shown below:

<u>Column 16</u>
Line 1, change "water into reaction vessel" to -- water into a reaction vessel --

Signed and Sealed this

Twenty-third Day of September, 2008

JON W. DUDAS
*Director of the United States Patent and Trademark Office*